United States Patent [19]

Lafon

[11] 4,407,822
[45] Oct. 4, 1983

[54] BENZAMIDO-ALKYL-HYDROXAMIC ACID DERIVATIVES

[75] Inventor: Louis Lafon, Paris, France

[73] Assignee: Laboratoire L. Lafon, Maisons Alfort, France

[21] Appl. No.: 360,056

[22] Filed: Mar. 19, 1982

[30] Foreign Application Priority Data

Mar. 25, 1981 [FR] France ............................... 81 06017

[51] Int. Cl.³ ..................... A61K 31/185; C07C 83/10
[52] U.S. Cl. .............................. 424/315; 260/500.5 H
[58] Field of Search ................. 260/500.5 H; 424/315

[56] References Cited

U.S. PATENT DOCUMENTS 3,728,380  4/1973  Johnson et al. ............. 260/500.5 H
4,083,996  4/1978  Tanaka et al. ............... 260/500.5 H
4,122,186  10/1978  Lafon ........................... 260/500.5 H Primary Examiner—J. E. Evans
Attorney, Agent, or Firm—Poms, Smith, Lande & Rose

[57] ABSTRACT

The present invention relates, as new industrial products, to 3-(aminobenzamido)-propionhydroxamic acids of formula:

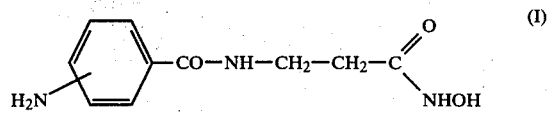

and their acid addition salts. These products are useful in therapeutics. The compounds of formula I may be prepared by catalytic hydrogenation of the corresponding 3-(nitro-benzamido)-propionhydroxamic acids.

2 Claims, No Drawings

BENZAMIDO-ALKYL-HYDROXAMIC ACID DERIVATIVES

The present invention relates, as new industrial products, to derivatives belonging to the family of benzamido-alkylhydroxamic acids. It also relates to the method for preparing same and to the use thereof in therapeutics, particularly as substances active on the CNS.

Belgian Pat. No. 852 738 discloses the hydrochloride of 2-(4-aminobenzamido)-acetohydroxamic acid, having Code No. CRL 40473 (ct. Example 18 of said Belgian Patent). It has now been unexpectedly found that the derivatives of formula I hereinafter, which are structurally different from the known product mentioned above, present very advantageous properties from the therapeutical standpoint, particularly as far as anti-aggressive properties are concerned.

According to the invention, a new benzamido-alkylhydroxamic acid derivative is recommended, characterised in that it is selected from the group consisting of (i) 3-(aminobenzamido)-propionhydroxamic acids of general formula:

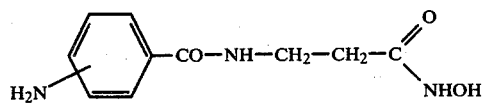

and (ii) acid addition salts thereof.

The invention is therefore directed to o-, m- and p-amino-benzamido-propionhydroxamic acids and their salts, the preferred products being 3-(3-amino-benzamido)-propionhydroxamic acid and addition salts thereof, particularly the hydrochloride.

Addition salts are understood here to mean the acid addition salts obtained by reaction of a free base of formula I with a mineral or organic acid. Among the acids which may be used for salifying the bases of formula I, particular mention may be made of hydrochloric, hydrobromic, nitric, sulfuric, acetic, propionic, oxalic, fumaric, maleic, succinic, benzoic, cinnamic, mandelic, citric, malic, tartric, p-toluene-sulfonic and methanesulfonic acids.

The compounds of formula I may be prepared according to a known method by application of conventional reaction mechanisms. For example, they may be prepared according to the modi operandi of Example 18 of the Belgian Patent mentioned above. The method for preparing a 3-(amino-benzamido)-propionhydroxamic acid recommended according to the invention is characterised in that a 3-(nitrobenzamido)-propionhydroxamic acid of formula:

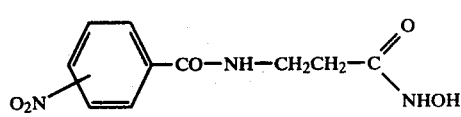

is subjected to a catalytic hydrogenation reaction by means of a catalysator constituted by palladium on carbon.

The compounds of formula I and their addition salts are useful in therapeutics on the CNS, particularly as sedative agents.

Finally, a therapeutical composition is recommended according to the invention which is characterised in that it contains, in association with a physiologically acceptable excipient, at least one compound of formula I or one of its non-toxic salts. Such a composition will of course contain a pharmaceutically effective amount of active ingredient.

Other advantages and features of the invention will be more readily understood on reading the following examples of preparation given by way of non-limiting example.

PREPARATION I

Obtaining of the hydrochloride of 3-(3-aminobenzamido)-propionhydroxamic acid

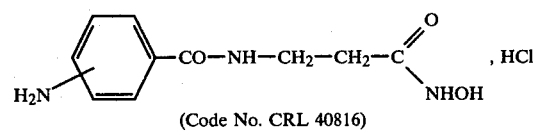

(Code No. CRL 40816)

(a) m-Nitrobenzamidopropionate of ethyl

A solution of 18.55 g (0.1 mol) of m-nitrobenzoyl chloride in 100 ml of benzene is poured dropwise under reflux in a solution of 15.35 g (0.1 mol) of hydrochloride of ethyl aminopropionate in 100 ml of benzene. Reflux is maintained for about 60 hours, the benzene phase is washed in water, with a solution of dilute bicarbonate, then with dilute HCl and again with water. It is dried over $Na_2SO_4$ and after evaporation, 24.4 g (yield: 91%) are collected of m-nitrobenzamido-propionate of ethyl which is in the form of a yellow-orange oil.

(b) m-nitrobenzamidopropionhydroxamic acid

A solution is prepared of sodium methylate with 4.22 g (0.183 gram-atom) of Na in 150 ml of anhydrous methanol and a quantity of 6.37 g (0.0917 mol) of hydrochloride of hydroxylamine in solution in 120 ml of anhydrous methanol is added cold. The sodium chloride formed is eliminated by filtration and 24.4 g (0.0917 mol) of m-nitrobenzamidopropionate of ethyl are added to the filtrate. After a night in contact at ambient temperature, the mixture is evaporated to dryness in vacuo, taken up in sufficient water to dissolve the sodium salt and acidified with concentrate HCl ($d_4^{15}=1.19$). The precipitate thus obtained is drained and washed in water. After recrystallization in water, 17.1 g (yield: 74%) of m-nitrobenzamidopropionhydroxamic acid are obtained.

(c) CRL 40816

A catalytic hydrogenation is carried out under reflux for 5 hours, from a mixture of 16.45 g of (0.065 mol) of m-nitrobenzamidopropionhydroxamic acid, 21 ml of cyclohexene, 2.2 g of Pd/carbon at 10% and 120 ml of anhydrous ethanol. The Pd/carbon is filtered, evaporated to dryness in vacuo and taken up in ethanol. The hydrochloride is precipitated by means of hydrochloric ethanol, then the precipitate is washed with a little ether. After recrystallization in a (10:90) v/v water-ethanol mixture, 10.7 g (yield: 64%) of CRL 40816 are obtained, which is in the form of a slightly pink powder, insoluble in alcohols, acetone, ether and very soluble in water. m.p.=206° C.

By proceeding as indicated hereinabove and replacing the chloride of m-nitrobenzoyl by the chlorides of o- and p-nitrobenzoyl, the 3-(2-aminobenzamido)- and 3-(4-aminobenzamido)-propionhydroxamic acids are respectively obtained.

The results of the tests undertaken with CRL 40816 are summarised hereinafter. In these tests, it was administered by the intraperitoneal route in a volume of 20 ml/kg in the male mouse and in a volume of 4 mg/kg in the male rat.

(1) Toxicity

The maximum non-lethal dose (LD-0) by the I.P. route in the male mouse is greater than 1024 mg/kg.

(2) Overall behaviour

Batches of 10 animals per dose are observed before, then 15 minutes, 30 minutes, 1 hour, 2 hours, 3 hours and 24 hours after I.P. administration of CRL 40816. It is observed (a) in the mouse that at a dose of 512 mg/kg, CRL 40816 provokes:
 (i) sedation with diminution of the reactivity to touch for 3 hours,
 (ii) a moderate hypothermia ($-1.3°$ C.) for 2 hours, and
 (iii) depressed respiration for 3 hours;
and
(b) in the rat, that, from a dose of 256 mg/kg, CRL 40816 brings about
 (i) a diminution of the reactivity to touch and muscular tonicity for 3 hours, and
 (ii) mydriasis for 3 hours.

(3) Action on the CNS (a) Interaction with apomorphine

In the mouse

Half and hour after administration of CRL 40816, batches of 6 mice receive a sub-cutaneous injection of apomorphine at the dose of 1 or 16 mg/kg. The following is observed: at low doses, the CRL 40816 does not modify the hypothermia, the attitude of verticalisation and the stereotypies induced by the apomorphine in the mouse; at the dose of 32 mg/kg, the CRL 40816 would appear to induce a discrete antagonism of the hypothermia induced by the lowest dose of apomorphine; at the highest dose (512 mg/kg), a substantial decrease of the temperature is observed further to the injection of CRL 40816.

in the rat

Batches of 6 rats receive the CRL 40816 half an hour before the sub-cutaneous injection of apomorphine at the dose of 0.5 mg/kg. It is observed that the CRL 40816 does not modify the stereotyped behaviour provoked by the apomorphine in the rat.

(b) Interaction with amphetamine

Half an hour after the administration of CRL 40816, batches of 6 rats receive an intraperitoneal injection of 2 mg/kg of amphetamine. It is observed that at high dose (256 mg/kg) the CRL 40816 brings about a moderate diminution of the intensity of the amphetaminic stereotypies.

(c) Interaction with reserpine

Four hours after the intraperitoneal injection of 2.5 mg/kg of reserpine, batches of 6 mice receive the CRL 40816. It is observed that the CRL 40816 does not modify the hypothermia nor the ptosis provoked by the reserpine.

(d) Interaction with oxotremorine

Oxotremorine (0.5 mg/kg - I.P.) is injected in batches of 6 mice half an hour after the administration of CRL 40816.

Action on temperature

At the dose of 32 mg/kg, the CRL 40816 appears to oppose the hypothermia-inducing action of oxotremorine moderately and slowly. On the other hand, at a high dose (512 mg/kg) the CRL 40816 exerts a hypothermia-inducing effect and aggravates the drop in temperature due to the oxotremorine.

Action on tremblings

The CRL 40816 leaves unchanged the tremblings produced by the oxotremorine.

Action on the peripheral cholinergic symptoms

The signs of peripheral cholinergic stimulation (salivation, lacrymation, defecation), which occur further to an injection of oxotremorine, are not modified by the CRL 40816.

(e) Action on the four-plate test, traction and electroshock

Batches of 10 mice were studied half an hour after the administration of CRL 40816.

It is observed that the CRL 40816 does not bring about an increase in the number of passages punished; it does not provoke any major motor incapacity and does not modify the convulsion-inducing and lethal effects of the electroshock.

(f) Action on spontaneous motility

Half an hour after having received the CRL 40816, the mice (6 per dose, 12 controls) were placed in an actimeter where their motility was recorded for 30 minutes.

At high dose (512 mg/kg), it is observed that the CRL 40816 brings about moderate hypomotility.

(g) Action on intergroup aggressiveness (comparative study)

After having dwelled for 3 weeks on either side of an opaque partition separating their cage through the centre, groups of 3 male mice (each mouse weighing about 20 g) receive the products to be tested (CRL 40816 and CRL 40473) by the I.P. route in solution in distilled water, at a rate of three cages per product and per dose and six cages for the control animals receiving only distilled water by the I.P. route. Half an hour later, the two groups of the same cage are brought together and the number of fights occurring in 10 minutes is noted. The results are shown in Table I hereinbelow and show that the CRL 40816 according to the invention (i) considerably reduces the number of fights at the dose of 128 mg/kg, (ii) completely eliminates fights at the dose of 512 mg/kg, and (iii) has a beneficial anti-agressive effect clearly greater than that of the CRL 40473 according to Example 18 of the Belgian Patent mentioned above.

TABLE I

| Product | dose (mg/kg) | number of fights per mouse | reduction of number of fights with respect to controls |
|---|---|---|---|
| controls | — | 3.13 | 0% |
| CRL 40816 | 128 | 1.44 | 54% |
| CRL 40816 | 512 | 0 | 100% |
| CRL 40473 | 128 | 2.25 | 28% |
| CRL 40473 | 512 | 1.82 | 41% |

(h) Action vis-à-vis some behaviours disturbed by various agents. Motility reduced by habituation to the cage After 18 hours dwelling in the actimeters, the mice (6 per dose, 12 controls) receive the CRL 40816. They are immediately put back in their respective cages and, half an hour later, their motility is recorded for 30 minutes.

It is observed that the CRL 40816 does not generally provoke any resumption of activity in the mouse habituated to its cage.

Motility reduced by hypoxic aggression

Half an hour after having received the CRL 40816, the mice (10 per dose, 20 controls) are subjected to an acute hypobar anoxia [depression of 600 mm Hg (or about $8 \times 10^4$ pascals) in 90 seconds, relaxation of 45 seconds], then they are placed in an actimeter where their motility is recorded for 10 minutes.

It is observed that the CRL 40816 does not bring about any improvement in the motor recovery in the mice whose motility was lowered further to a brief spell in a cage at reduced pressure.

Asphyxic anoxia

Half an hour after administration of CRL 40816, batches of 10 mice receive an intraperitoneal injection of 32 mg/kg of gallamine triiodoethylate.

It will be noted that at the highest dose used (512 mg/kg), the CRL 40816 delayed the occurrence of convulsions and death consecutive to an asphyxic anoxia provoked by a blocking (curarisation) agent such as gallamine triiodoethylate.

In conclusion, the tests on the CNS show that the CRL 40816 presents sedative properties at high dose: hyporeactivity, hypomotility and hypothermia, which explain the resistance to anoxia on the one hand and the diminution of aggressiveness and amphetaminic stereotypies on the other hand. Moreover, the results observed at 32 mg/kg (partial antagonism of the hypothermia induced by oxotremorine, by the small dose of apomorphine, the moderate increase in the number of passages punished in the four plate test and the slight improvement in the motor recovery after hypobar hypoxia) enable the CRL 40816 to be differential from the products described previously.

In clinic, the CRL 40816 has proved to be an excellent antidepressant in human beings, in the form of tablets or capsules each containing 200 mg of active ingredient, at a rate of 2 tablets or capsules per day.

What is claimed is:

1. 3-(3-aminobenzamido)-propionhydroxamic acid and its acid addition salts.

2. A therapeutical composition comprising, in association with a physiologically acceptable excipient, a pharmaceutically effective amount of a compound according to claim 1.

* * * * *

UNITED STATES PATENT AND TRADEMARK OFFICE
CERTIFICATE OF CORRECTION

PATENT NO. : 4,407,822
DATED : October 4, 1983
INVENTOR(S) : Louis Lafon

It is certified that error appears in the above-identified patent and that said Letters Patent are hereby corrected as shown below:

In column 1, line 13 "ct." should be --c.f.--

In column 2, line 32 "60 hours" should be --6 hours--

In column 3, line 36 "and" should be --an--

In column 6, line 16 "differential" should be --differentiated--.

Signed and Sealed this

Eighth Day of May 1984

[SEAL]

Attest:

Attesting Officer

GERALD J. MOSSINGHOFF

Commissioner of Patents and Trademarks